(12) United States Patent
Gao et al.

(10) Patent No.: US 11,911,552 B2
(45) Date of Patent: Feb. 27, 2024

(54) COMBINED BIO-ARTIFICIAL LIVER SUPPORT SYSTEM

(71) Applicant: Southern Medical University Zhujiang Hospital, Guangdong (CN)

(72) Inventors: Yi Gao, Guangdong (CN); Mingxin Pan, Guangdong (CN); Lei Feng, Guangdong (CN); Yang Li, Guangdong (CN); Lei Cai, Guangdong (CN); Guolin He, Guangdong (CN); Jun Weng, Guangdong (CN); Qing Peng, Guangdong (CN)

(73) Assignee: Southern Medical University Zhujiang Hospital (CN)

( * ) Notice: Subject to any disclaimer, the term of this patent is extended or adjusted under 35 U.S.C. 154(b) by 841 days.

(21) Appl. No.: 16/966,101

(22) PCT Filed: Mar. 23, 2018

(86) PCT No.: PCT/CN2018/080285
§ 371 (c)(1),
(2) Date: Jul. 30, 2020

(87) PCT Pub. No.: WO2019/148611
PCT Pub. Date: Aug. 8, 2019

(65) Prior Publication Data
US 2021/0030943 A1 Feb. 4, 2021

(30) Foreign Application Priority Data
Feb. 1, 2018 (CN) .......................... 201810102479.8

(51) Int. Cl.
*A61M 1/16* (2006.01)
*A61M 1/34* (2006.01)
(Continued)

(52) U.S. Cl.
CPC ........ *A61M 1/3689* (2014.02); *A61M 1/1698* (2013.01); *A61M 1/3623* (2022.05);
(Continued)

(58) Field of Classification Search
CPC .............. A61M 1/3472; A61M 1/3482; A61M 1/3486; A61M 1/3489; A61M 1/1698;
(Continued)

(56) References Cited

U.S. PATENT DOCUMENTS 4,209,392 A * 6/1980 Wallace ................. B01D 15/00
210/321.83
5,270,192 A * 12/1993 Li .......................... C12M 29/10
435/174

(Continued)

FOREIGN PATENT DOCUMENTS

CN     1330959 A      1/2002
CN   201033178 Y *   3/2008

(Continued)

OTHER PUBLICATIONS

International Search Report for Application No. PCT/CN2018/080285 dated Jun. 13, 2018, 2 pages.

(Continued)

*Primary Examiner* — Susan S Su
*Assistant Examiner* — Ted Yang
(74) *Attorney, Agent, or Firm* — Lerner David LLP (57) ABSTRACT

A combined bio-artificial liver support system, includes branch tubes that are connected in sequence: a blood input branch tube, an upstream tail end, a first plasma separation branch tube comprising at least a first plasma separator, a non-biological purification branch tube comprising at least a plasma perfusion device and a bilirubin adsorber, a biological purification branch tube comprising at least a hepatocyte (Continued)

culture cartridge assembly, and a plasma return branch tube, a downstream tail end of which is set as a blood output end.

14 Claims, 5 Drawing Sheets

(51) Int. Cl.
  *A61M 1/36* (2006.01)
  *A61M 39/10* (2006.01)
  *C12M 3/00* (2006.01)
(52) U.S. Cl.
  CPC ........ *A61M 1/3626* (2013.01); *A61M 1/3653* (2013.01); *A61M 1/3679* (2013.01); *A61M 39/105* (2013.01); *C12M 21/08* (2013.01); *A61M 1/3496* (2013.01); *A61M 1/3672* (2013.01); *A61M 2202/0415* (2013.01); *A61M 2205/3368* (2013.01)
(58) Field of Classification Search
  CPC .... A61M 1/3679; A61M 1/14; A61M 1/3689; A61M 1/3626; A61M 1/3653; A61M 39/105; A61M 1/3496; A61M 1/3672; A61M 2202/0415; A61M 2205/3368; C12M 21/08
  See application file for complete search history.

(56) References Cited

U.S. PATENT DOCUMENTS

| | | | | |
|---|---|---|---|---|
| 5,277,820 A * | 1/1994 | Ash | ............... | A61M 1/3434 210/651 |
| 5,368,555 A * | 11/1994 | Sussman | ............... | A61M 1/3475 435/1.1 |
| 5,536,412 A * | 7/1996 | Ash | ............... | A61M 60/546 210/651 |
| 6,858,146 B1 * | 2/2005 | Myers | ............... | A61M 1/1627 435/402 |
| 7,291,122 B2 * | 11/2007 | Matson | ............... | A61M 1/342 210/651 |
| 7,520,992 B2 * | 4/2009 | Radunsky | ............... | A61M 1/3486 604/19 |
| 2002/0188240 A1 * | 12/2002 | Gorsuch | ............... | A61M 1/3679 604/6.04 |
| 2003/0017142 A1 * | 1/2003 | Toner | ............... | C12M 29/04 435/370 |
| 2003/0228685 A1 * | 12/2003 | Nyberg | ............... | A61M 1/3489 435/297.1 |
| 2004/0228829 A1 * | 11/2004 | Roberts | ............... | A61M 1/3679 604/500 |
| 2005/0006296 A1 * | 1/2005 | Sullivan | ............... | A61M 1/3493 210/512.1 |
| 2005/0015040 A1 * | 1/2005 | Wuepper | ............... | A61M 1/3681 604/5.01 |
| 2005/0182349 A1 * | 8/2005 | Linde | ............... | A61M 1/3489 604/4.01 |
| 2005/0236329 A1 * | 10/2005 | Brotherton | ............... | A61M 1/3472 210/651 |
| 2006/0186044 A1 * | 8/2006 | Nalesso | ............... | A61M 1/3486 210/651 |
| 2007/0289928 A1 * | 12/2007 | Umehara | ............... | A61M 1/3465 210/805 |
| 2011/0105982 A1 * | 5/2011 | Leonard | ............... | A61M 1/14 604/6.01 |
| 2012/0009086 A1 * | 1/2012 | Nyberg | ............... | A61M 1/3489 422/44 |
| 2013/0102948 A1 * | 4/2013 | Reich | ............... | A61M 1/3615 210/641 |
| 2013/0270185 A1 * | 10/2013 | Kreymann | ............... | A61M 1/3623 210/639 |
| 2015/0290380 A1 * | 10/2015 | Welzel | ............... | A61M 1/3472 210/638 |
| 2016/0022895 A1 * | 1/2016 | Okahisa | ............... | A61M 1/3482 210/195.1 |
| 2018/0117235 A1 * | 5/2018 | Zhou | ............... | C12M 29/10 |
| 2018/0303995 A1 * | 10/2018 | Stange | ............... | A61M 1/3679 |
| 2019/0030232 A1 * | 1/2019 | Kreymann | ............... | A61M 1/3666 |
| 2019/0192757 A1 * | 6/2019 | Kreymann | ............... | A61M 1/3479 |

FOREIGN PATENT DOCUMENTS

| | | | | |
|---|---|---|---|---|
| CN | 101455864 A | * | 6/2009 | |
| CN | 101455864 A | | 6/2009 | |
| CN | 201320317 Y | * | 10/2009 | |
| CN | 202699700 U | | 1/2013 | |
| CN | 104147652 A | | 11/2014 | |
| CN | 104800902 A | * | 7/2015 | |
| CN | 104800902 A | | 7/2015 | |
| CN | 104958795 A | * | 10/2015 | ......... A61M 1/1627 |
| CN | 105087380 A | | 11/2015 | |
| CN | 105457115 A | | 4/2016 | |
| CN | 106267397 A | | 1/2017 | |
| CN | 107583120 A | | 1/2018 | |
| CN | 108211032 A | * | 6/2018 | ......... A61M 1/1698 |
| CN | 208770520 U | | 4/2019 | |
| WO | WO-02087661 A1 | * | 11/2002 | ......... A61M 1/3472 |
| WO | WO-03094998 A1 | * | 11/2003 | ............. A61M 1/16 |
| WO | WO-2008051994 A2 | * | 5/2008 | ......... A61M 1/3472 |
| WO | WO-2010058583 A1 | * | 5/2010 | ......... A61M 1/3472 |

OTHER PUBLICATIONS

Hu Wei, Gu Han-qing, "Progress on Artificial Liver Support Devices", Chinese J. Dial. & Artif. Organs vol. 21 No. 4 Dec. 2010. 10 pgs.

* cited by examiner

COMBINED BIO-ARTIFICIAL LIVER SUPPORT SYSTEM

CROSS-REFERENCE TO RELATED APPLICATIONS

The present application is a national phase entry under 35 U.S.C § 371 of International Application No. PCT/CN2018/080285 filed Mar. 23, 2018, which claims priority from Chinese Application No. 201810102479.8 filed Feb. 1, 2018, all of which are hereby incorporated herein by reference.

FIELD OF THE INVENTION

The present invention mainly relates to the field of biology and medical devices, in particular to a support system for an artificial liver with combined functions.

BACKGROUND OF THE INVENTION

China is a country with a high incidence of liver disease, and liver disease will eventually develop into liver failure. Due to liver failure, patients have a high death rate and treatment is difficult. Clinically, liver transplantation is currently the most effective treatment for liver disease. However, due to scarcity of donors, high cost, and rejection of the human body's own immune system, the application of liver transplantation is limited. At the same time, while waiting for liver transplantation, the patient is still suffering from liver failure. The patient's physique and healthy condition may be affected, making liver transplantation unsuitable.

At present, artificial liver can partially or longer extend the life of patients who are not suitable for liver transplantation, and improve the quality of life. It can also provide disease control, liver deterioration delay, and improvement of surgery success rate for patients who are waiting for donors and preparing for liver transplantation. In the prior art, the function realized by the artificial liver is relatively simple, mainly for the purpose of purification, to eliminate the accumulation of toxins caused by the loss or reduction of metabolic function in the blood of the patient due to the impaired liver function. The prior art artificial liver cannot handle the comprehensive situation of patients with severe liver failure due to its single function. The patient needs to replace multiple machines, which results in increased costs for the patient and also increases the patient's physical burden and psychological pressure. Switching between multiple machines will also increase the learning cost of technicians, increase the difficulty of operation and the need for operating space.

The present invention aims to provide a new combined bio-artificial liver support system, which can realize the switching of multiple functions.

SUMMARY OF THE INVENTION

The present invention provides a combined bio-artificial liver support system, comprising a plurality of branch tubes that are connected in sequence: a blood input branch tube, an upstream tail end of which is set as a blood input end, a first plasma separation branch tube comprising at least a first plasma separator, a non-biological purification branch tube comprising at least a plasma perfusion device and a bilirubin adsorber, a biological purification branch tube comprising at least a hepatocyte culture cartridge assembly, and a plasma return branch tube, a downstream tail end of which is set as a blood output end. By means of a three-way device, the first plasma separation branch tube is connected to inlet ends of the biological purification branch tube and the non-biological purification branch tube, an outlet end of the non-biological purification branch tube is connected to the biological purification branch tube, and the outlet end of the non-biological purification branch tube is connected to the plasma return branch tube, the three-way device comprises a three-way joint and branches respectively connected to the three-way joint, and at least two said branches are respectively provided with a flow restricting member and a coupling member.

Preferably, the first plasma separation branch tube comprises: a first plasma separator provided with a blood inlet, a plasma outlet, and a blood cell outlet, a plasma separation pump connected to the plasma outlet through a conduit, a plasma separation branch tube extending downstream from the plasma separation pump, and a first three-way device connected to an end of the plasma separation branch tube of the first three-way device, the plasma separation branch tube is directly connected to a first three-way joint of the first three-way device, and the remaining branches extending from the first three-way joint are provided with the flow restricting members and the coupling members.

Preferably, the non-biological purification branch tube comprises: a plasma perfusion device provided with a perfusion inlet and a perfusion outlet, a bilirubin adsorber connected to the perfusion outlet through a conduit, a first purification branch extending downstream from the bilirubin adsorber and a second three-way device connected to an end of the first purification branch, and the remaining branches extending from the second three-way joint are provided with the flow restricting members and the coupling members.

Preferably, the biological purification branch tube comprises: an oxygenator provided with an oxygenation outlet, a circulation pump connected to the oxygenation outlet, and a hepatocyte culture cartridge assembly connected to the circulation pump through a circulation branch, a plasma return pump connected to the hepatocyte culture cartridge assembly, and a plasma return branch extending from the plasma return pump to a downstream.

Preferably, the plasma return branch comprises at least: a blood cell mixer connected to the blood cell outlet and provided with a whole blood outlet, and a bubble monitor connected to the whole blood outlet, the bubble monitor is also connected to the blood output end, and a third three-way device is connected to an upstream end of the plasma return branch tube, the plasma return branch tube is directly connected to a third three-way joint of the third three-way device, an upstream extension branch of the third three-way joint is connected to the first purification branch and the plasma return branch through the flow restricting member and the coupling members respectively.

Preferably, a second plasma separation branch tube is further provided between the biological purification branch tube and the plasma return branch tube, the second plasma separation branch tube includes at least a second plasma separator provided with a second plasma inlet, a second plasma outlet, and a cell outlet, the second plasma inlet is connected to the hepatocyte culture cartridge assembly, and the second plasma outlet is connected to the plasma return branch tube.

Preferably, the cell outlet is connected to a liquid storage bottle for depositing cells or cell debris and adjusting the flow rate difference, and the liquid storage bottle is also connected to the inlets of the oxygenation outlet and the circulation pump.

Preferably, the cell outlet is connected to a second chamber of the liquid storage bottle, and a partition is provided between a first chamber and the second chamber for isolating the deposited cells and cell debris.

Preferably, the hepatocyte culture cartridge assembly comprises a hepatocyte culture cartridge body and a circulation tube connected by a conduit and a valve assembly, an inlet of the circulation tube is connected to the circulation pump, and an outlet of the circulation tube is connected to the plasma return branch tube.

Preferably, the valve assembly comprises a first valve, a second valve, a third valve, and a fourth valve, the circulation tube includes a first circulation tube connected to the first valve, a second circulation tube connected to the second valve, a third circulation tube connected to the third valve, and the fourth circulation tube connected to the fourth valve, the first circulation tube and the second circulation tube are connected through a first interface, and the first interface is connected to the circulation branch, the third circulation tube and the fourth circulation tube are connected through a second interface, and the second interface is connected to the plasma return pump, the first circulation tube and the third circulation tube are connected through a third interface, and the third interface is connected to one end of the hepatocyte culture cartridge assembly, the second circulation tube and the fourth circulation tube are connected through a fourth interface, and the fourth interface is connected to the other end of the hepatocyte culture cartridge assembly.

Preferably, the fluid flow directions of the third interface and the fourth interface are opposite.

Preferably, the branch of the three-way device and the branch tubes connected to it are connected by at least one connection mode of screw connection assembly connection and sleeve member connection.

Preferably, the connection structure of the screw connection assembly comprises: the branches tapped with an external thread, and a conduit of the branch tube tapped with an internal thread matching the external thread at one end.

Preferably, a connection location between the conduit and the branch is also provided with a sleeve which provides resistance for rotation of the branch tube and the branch and enhances the sealing performance.

The invention provides a combined bio-artificial liver support system, which can better solve the technical problems and has the following advantages:

(1) According to the combined bio-artificial liver support system related to the present invention controls the on and off of different branch tubes through a three-way device, so that the support system enters different modes, which facilitates targeted blood differentiation handling;

(2) According to the combined bio-artificial liver support system related to the present invention, by adjusting the number and position of the three-way device, it is also possible to add or delete branch tubes with different functions to further adjust the integrated functions of the support system;

(3) A combined bio-artificial liver support system related to the present invention can realize multiple fluid flowing manners in the hepatocyte culture cartridge assembly by reasonably arranging the circulation tubes of the hepatocyte culture cartridge assembly and reasonably controlling the on and off of the valve assembly; and (4) According to the combined bio-artificial liver support system related to the present invention, the temperature regulators arranged in different tubes can maintain the support system, the fluid in the system, the liver cell culture cartridge assembly, etc. within the body temperature range, and provide control of different temperature ranges for the branch tubes with different functions.

BRIEF DESCRIPTION OF THE DRAWINGS

The above and/or additional aspects and advantages of the present invention will become apparent and easy to understand from the following description of the embodiments in conjunction with the accompanying drawings, in which.

DETAILED DESCRIPTION OF THE INVENTION

The embodiments of the present invention are described in detail below, and examples of the embodiments are shown in the drawings. The embodiments described below with reference to the drawings are exemplary, and are only used to explain the present invention, and cannot be construed as limiting the present invention. In order to facilitate the demonstration of the practical application of the combined bio-artificial liver support system, the following embodiments will introduce specific components of the support system, so that the connective relationship between the application of the support system and the components of the support system is more fully displayed and easy to understand, it is worth noting that the scope of protection of the present invention is not such limited.

Please refer to FIG. 1, which shows the overall structure of a combined bio-artificial liver support system 1 (hereinafter referred to as "support system 1") provided by this embodiment. The support system 1 includes at least a plurality of interconnected branch tubes. The branch tubes include: a blood input branch tube 11, an upstream tail end of which is set as a blood input end 111, a first plasma separation branch tube 12 comprising at least a first plasma separator 121, a non-biological purification branch tube 13 comprising at least a plasma perfusion device 131 and a bilirubin adsorber 132, a biological purification branch tube 14 comprising at least a hepatocyte culture cartridge assembly 141, and a plasma return branch tube 15, a downstream tail end of which is set as a blood output end 151. By means of a three-way device 16, the first plasma separation branch tube 12 is connected to inlet ends of the biological purification branch tube 14 and the non-biological purification branch tube 13, an outlet end of the non-biological purification branch tube 13 is connected to the biological purification branch tube 14, and the outlet end of the non-biological purification branch tube 13 is connected to the plasma return branch tube 15. Please refer to FIG. 7, the three-way device 16 comprises a three-way joint 161 and branches respectively connected to the three-way joint 161, wherein at least two branches are respectively provided with a flow restricting member and a coupling member. Preferably, the branch includes a first branch 162-1, a second branch 162-2 and a third branch 162-3. The second branch 162-2 and the third branch 162-3 are respectively provided with a pinch valve 163 and a screw connection assembly 164. In other possible implementation manners, the pinch valve 163 may be replaced by or used in combination with a non-return valve, a roller valve, or other valves that control the flow rate and the on-off of conduits. The three-way joint 161 is connected to the first branch 162-1 as well as the second branch 162-2 and the third branch 162-3, both of which are the branches of the first branch 162-1. The fluid is split or merged in the three-way joint 161, and flows from the first branch 162-1 into the second branch 162-2, the third branch 162-3, or flows from the second branch 162-2, the third branch 162-3 into the first branch 162-1. In this embodiment, in order to better control the blood input end 111 and the blood output end 151, an input end valve 111-1 for controlling the opening and closing of the blood input branch tube 11 is provided downstream of a conduit near the blood input end 111. An outlet valve 151-1 for controlling the opening and closing of the plasma return branch tube 15 is provided downstream of a conduit near the blood output end 151. In case of emergencies, the operator can close the input valve 111-1 and the output valve 151-1 in time, which can protect the safety of the support system and the patient. In this embodiment, the input valve 111-1 and the output valve 151-1 may be pinch valves.

Figure 7:
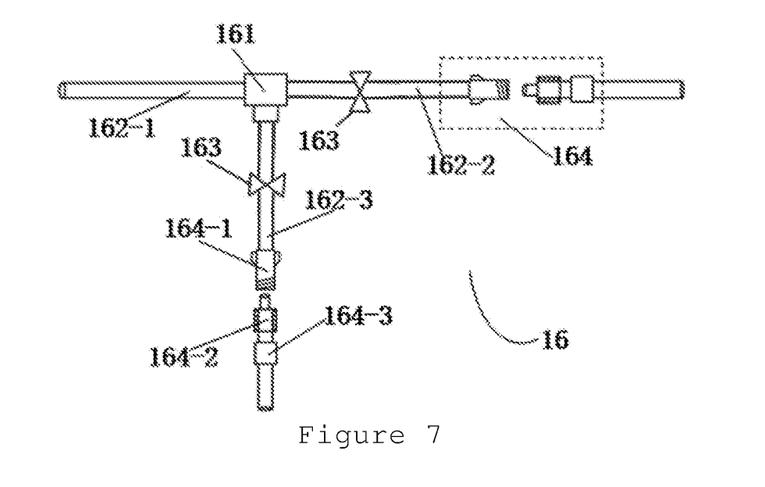
FIG. 7 is a structural view of a three-way device of the present invention.

Please continue to refer to FIG. 7. Specifically, the screw connection assembly 164 includes a tube end 164-1 located on the second branch 162-2 or on the third branch 162-3 and having an external thread. It also includes a branch tube conduit 164-2 with an internal thread at the other end. The external thread and the internal thread match each other. More specifically, the screw connection assembly 164 further includes a sleeve 164-3, which is screwed on the tube end 164-1 and the branch tube conduit 164-2 to provide appropriate resistance, helping users to fasten the conduits quickly during use, and avoiding the user from slipping due to wet hands and slippery tubes. The sleeve 164-3 can also cover the connection between the tube end 164-1 and the branch tube conduit 164-2 after fastening, to play a role of auxiliary connection and sealing and leakage prevention. The sleeve 164-3 can be made of soft and elastic materials, such as rubber, silicone, plastic, etc. In other possible embodiments, at least one of the tube end 164-1 and the branch tube conduit 164-2 is provided with a wing-shaped protrusion, which is convenient for the user to apply a force. For similar structure of the subsequent three-way devices 16, such as a first three-way device 16A, a second three-way device 16B, and a third three-way device 16C, please refer to the above structure.

Figure 1:
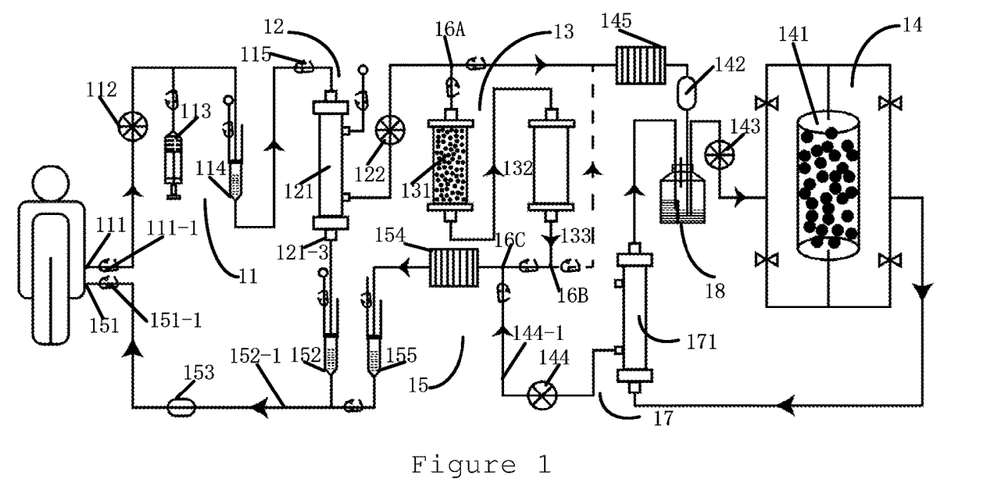
FIG. 1 is an overall structure view of a combined bio-artificial liver support system according to the present invention.
Figure 3:
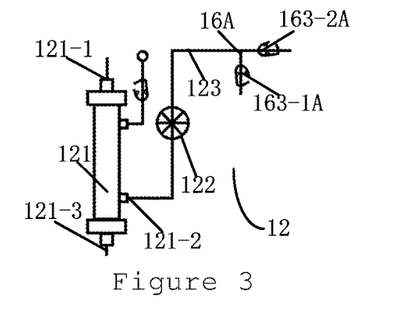
FIG. 3 is a structural view of a first plasma separation branch tube according to the present invention.

Specifically, please refer to FIGS. 1 and 3, the first plasma separation branch tube 12 includes: a first plasma separator 121 provided with a blood inlet 121-1, a plasma outlet 121-2, and a blood cell outlet 121-3, a plasma separation pump 122 connected to the plasma outlet 121-2 through a conduit, a plasma separation branch tube 123 extending downstream from the plasma separation pump 122, and a first three-way device 16A connected to an end of the plasma separation branch tube 123 of the first three-way device 16A. Here, the plasma separation branch tube 123 is directly connected to a first three-way joint of the first three-way device 16A. A pinch valve 163 and a screw connection assembly 164 are provided on a branch tube extending from the first three-way joint. Please refer to FIG. 7, regarding the specific structure of the first three-way device 16A, please refer to the three-way device 16, regarding the specific structure of the first three-way joint, please refer to the three-way joint 161, and regarding the branch that the first three-way joint extends, please refer to the second branch 162-2 and the third branch 162-3. In the pinch valve 164 of the first plasma separation branch tube 12, a pinch valve 163-1A and a pinch valve 163-2A respectively control the opening and closing of different branches.

Figure 4:
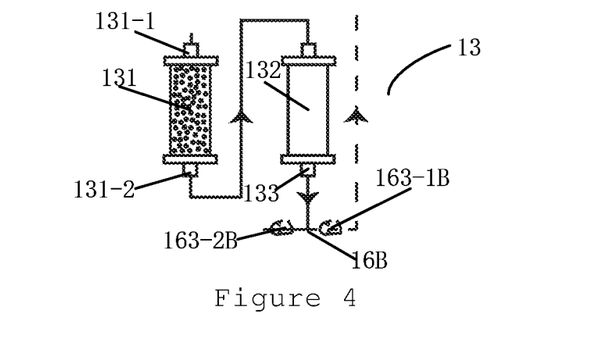
FIG. 4 is a structural view of a non-biological purification branch tube of the present invention.

More specifically, please refer to FIG. 1 and FIG. 4. The non-biological purification branch tube 13 includes: a plasma perfusion device 131 provided with a perfusion inlet 131-1 and a perfusion outlet 131-2, a bilirubin adsorber 132 connected to the perfusion outlet 131-2 through a conduit, a first purification branch 133 extending downstream from the bilirubin adsorber 132 and a second three-way device 16B connected to an end of the first purification branch 133. The first purification branch 133 directly communicates with a second three-way joint of the second three-way device 16B. A pinch valve 163 and a screw connection assembly 164 are provided on a branch extending from the second three-way joint. Please refer to FIG. 7, regarding the specific structure of the second three-way device 16B, please refer to the three-way device 16, regarding the specific structure of the second three-way joint, please refer to the three-way joint 161, and regarding the branch that the second three-way joint extends, please refer to the second branch 162-2 and the third branch 162-3. In a pinch valve 164 of the non-biological purification branch tube 13, a pinch valve 163-1B and a pinch valve 163-2B respectively control opening and closing of different branches.

Figure 5:
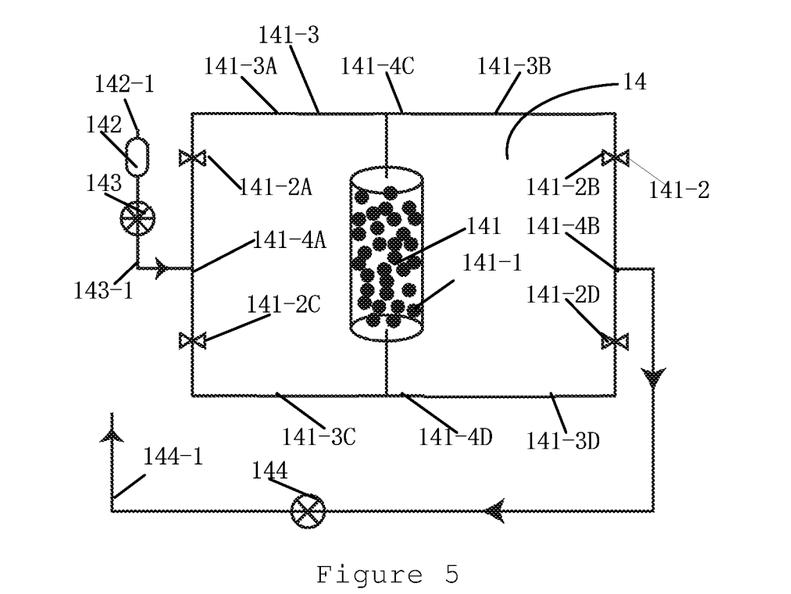
FIG. 5 is a structural view of a biological purification branch tube of the present invention.

For further details, please refer to FIGS. 1 and 5. The biological purification branch tube 14 includes: an oxygenator 142 provided with an oxygenation outlet 142-1, a circulation pump 143 connected to the oxygenation outlet 142-1, and a hepatocyte culture cartridge assembly 141 connected to the circulation pump 143 through a circulation branch 143-1, a plasma return pump 144 connected to the hepatocyte culture cartridge assembly 141, and a plasma return branch 144-1 extending from the plasma return pump 144 to a downstream.

Figure 6:
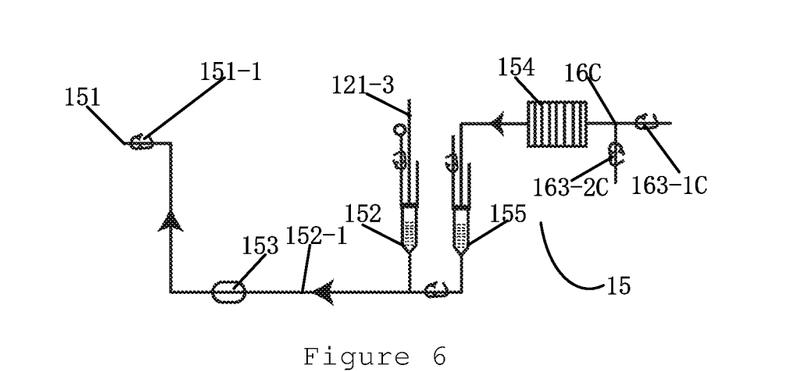
FIG. 6 is a structural view of a plasma return branch tube of the present invention.

More specifically, please refer to FIG. 1 and FIG. 6. In this embodiment, the plasma return branch 15 includes at least: a blood cell mixer 152 connected to the blood cell outlet 121-3 and provided with a whole blood outlet 152-1, and a bubble monitor 153 connected to the whole blood outlet 152-1. The bubble monitor 153 is also connected to the blood output end 151, and a third three-way device 16C is connected to an upstream end of the plasma return branch tube 15. Here, the plasma return branch tube 15 is directly connected to a third three-way joint of the third three-way device 16C. A pinch valve 163 and a screw connection assembly 164 are provided on the branch extending from the third three-way joint. Please refer to FIG. 7, regarding the specific structure of the third three-way device 16C, please refer to the three-way device 16, regarding the specific structure of the third three-way joint, please refer to the three-way joint 161, and regarding the branch that the third three-way joint extends, please refer to the second branch 162-2 and the third branch 162-3. In the pinch valve 164 of the plasma return branch tube 15, a pinch valve 163-1C and a pinch valve 163-2C respectively control the opening and closing of different branches. In this embodiment, the plasma return branch tube 15 is connected to the non-biological purification branch tube 13 through a pinch valve 163-1C. The plasma return branch tube 15 is connected to the biological purification branch tube 14 through a pinch valve 163-2C. In this embodiment, since the distance between the pinch valve 163-1C and the pinch valve 163-2B is relatively short, and the control branch is the same, and therefore, in this embodiment, the pinch valve 163-1-1C is combined with pinch valve 163-2B, and only one pinch valve is used.

Figure 8:
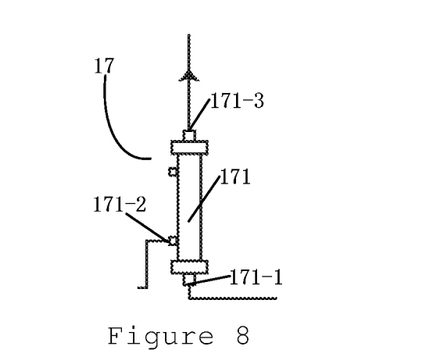
FIG. 8 is a structural view of a second plasma separation branch tube according to the present invention.

More specifically, please refer to FIGS. 1 and 8, a second plasma separation branch tube 17 is further provided between the biological purification branch tube 14 and the plasma return branch tube 15. In this embodiment, the second plasma separation branch tube 17 includes at least a second plasma separator 171 provided with a second plasma inlet 171-1, a second plasma outlet 171-2, and a cell outlet 171-3. The second plasma inlet 171-1 is connected to the hepatocyte culture cartridge assembly 141, and the second plasma outlet 171-2 is connected to the plasma return branch tube 15. In this embodiment, the second plasma outlet 171-2 is connected to the plasma return branch tube 15 by connecting the plasma return pump 144 and further through the plasma return branch 144. It is worth noting that the input of the cell outlet 171-3 in this embodiment is a plasma mixture that may be mixed with impurities such as cells, cell debris, bubbles, etc., and is not limited to cells.

Figure 9:
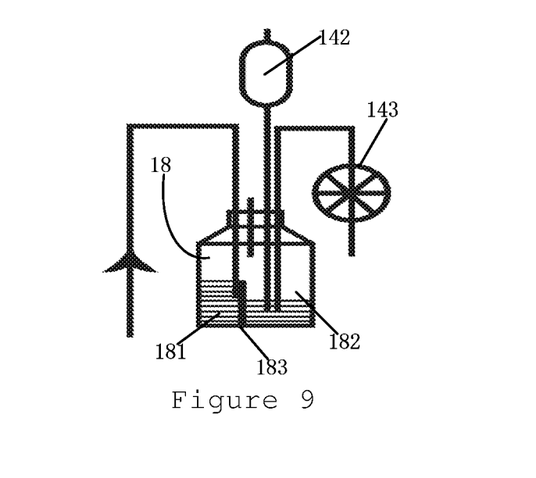
FIG. 9 is a structural view of a liquid storage bottle according to the present invention.

More specifically, please refer to FIGS. 1 and 9. The cell outlet 171-3 is connected to a liquid storage bottle 18 for depositing cells or cell debris and adjusting the flow rate difference. The liquid storage bottle 18 is also connected to the inlets of the oxygenation outlet 142-1 and the circulation pump 143. The cell outlet 171-3 is connected to a second chamber 182 of the liquid storage bottle 18. A partition 183 is provided between a first chamber 181 and the second chamber 182 for isolating the deposited cells and cell debris.

After the plasma mixture enters the first chamber 181 of the liquid storage bottle 18, under the action of gravity or other external forces, impurities in the plasma mixture begin to settle. The supernatant is relatively pure plasma. After a certain time of accumulation, the position of the plasma will get higher than the highest point of the partition 183, and the plasma then will flow into the second chamber 182, and enter the hepatocyte culture cartridge assembly 141 through the circulation pump 143. The second plasma separator 171 is in communication with the liquid storage bottle 18, which can improve the utilization rate of plasma and avoid excessive waste of plasma after plasma is separated. It also prevents cell debris from clogging the catheters or branch tubes, causing local pressure to rise sharply. In other possible implementation manners, the partition 183 can also be replaced with a filter mesh or a filter membrane, so as to filter out pure plasma quickly and in real time and let the plasma enter the circulation pump 143. In addition, the liquid storage bottle 18 can also balance the flow rate in the support system 1.

More specifically, referring to FIGS. 1 and 5, the hepatocyte culture cartridge assembly 141 includes a hepatocyte culture cartridge body 141-1 and a circulation tube 141-3 connected by a conduit and a valve assembly 141-2. An inlet of the circulation tube 141-3 is connected to the circulation pump 143, and an outlet of the circulation tube 141-3 is connected to the plasma return branch tube 15 through the plasma return pump 144 and the plasma return branch 144-1.

More specifically, please continue to refer to FIG. 5, and the valve assembly 141-2 includes a first valve 141-2A, a second valve 141-2B, a third valve 141-2C, and a fourth valve 141-2D. The circulation tube 141-3 includes a first circulation tube 141-3A connected to the first valve 141-2A, a second circulation tube 141-3B connected to the second valve 141-2B, a third circulation tube 141-3C connected to the third valve 141-2C, and the fourth circulation tube 141-3D connected to the fourth valve 141-2D. The first circulation tube 141-3A and the second circulation tube 141-3B are connected through a first interface 141-4A, and the first interface 141-4A is connected to the circulation branch 143-1. The third circulation tube 141-3C and the fourth circulation tube 141-3D are connected through a second interface 141-4B, and the second interface 141-4B is connected to the plasma return pump 144. The first circulation tube 141-2A and the third circulation tube 141-2C are connected through a third interface 141-4C, and the third interface 141-4C is connected to one end of the hepatocyte culture cartridge body 141-1. The second circulation tube 141-2B and the fourth circulation tube 141-2D are connected through a fourth interface 141-4D, and the fourth interface 141-4D is connected to the other end of the hepatocyte culture cartridge body 141-1. More specifically, the fluid flow directions of the third interface 141-4C and the fourth interface 141-4D are opposite.

Figure 2:
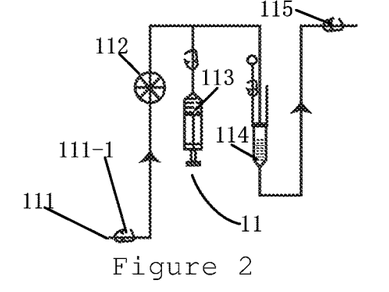
FIG. 2 is a structural view of a blood input branch tube according to the present invention.

In this embodiment, in addition to a blood input end 111, the blood input branch tube 11 also includes a blood pump 112, a drug infusion device 113 connected in parallel to the blood input branch tube 11, a blood mixer 114 connected in series in the blood input branch tube 11, and a check valve 115 to prevent liquid from flowing back. In other possible implementation manners, the drug infusion device 113 may select a quantitative or timed device such as a syringe to inject the drug into the blood input branch tube 11. In this embodiment, the drug input by the drug infusion device 113 is an anticoagulant drug to prevent blood clotting. More specifically, the anticoagulant drug in this embodiment uses heparin. In other possible implementations, the anticoagulant drug may also use natural anticoagulant heparin such as hirudin, or at least one of potassium salts such as sodium citrate and potassium fluoride and calcium ion chelating agents such as EDTA.

In other possible implementation manners, the support system 1 is further provided with a temperature regulator. In this embodiment, a first temperature regulator 145 is provided between the pinch valve 163-2A and the oxygenation outlet 142-1. A second temperature regulator 154 is provided at a position close to the third three-way device 16C in the plasma return branch tube 15. The first temperature regulator 145 and the second temperature regulator 154 not only have a heating function, but also have a cooling function. They are mainly responsible for adjusting the fluid in the catheter to a suitable temperature range for the human body, or maintaining a stable and fluid state of the fluid. It avoids changes in temperature or changes in physical and chemical properties of fluid caused by extreme temperatures. The temperature regulators can realize refined and regional temperature adjustment of all or part of the support system 1 through changes in number and position. In addition, when conditions permit, you can also use incubators, water bath constant temperature and other means to adjust the temperature. In the plasma return separation branch tube 15, a plasma homogenizer 155 is also provided between the second temperature regulator 154 and a cell mixer 152. After the second temperature regulator 154 adjusts the temperature of the plasma, the plasma is prone to changes in physical and chemical properties such as stratification, turbidity, precipitation, etc. The plasma homogenizer 155 can be added to homogenize the plasma before mixing the whole blood to improve the quality of whole blood mixing.

In this embodiment, the support system 1 controls the three-way device 16 (including the first three-way device 16A, the second three-way device 16B, and the third three-way device 16C in this embodiment), and further controls the on and off of the branch tubes, and the support system 1 can at least have the following modes: non-biological purification mode, biological purification mode, and mixing mode. The operation of the support system 1 will be described in detail below in combination with different modes.

Figure 10:
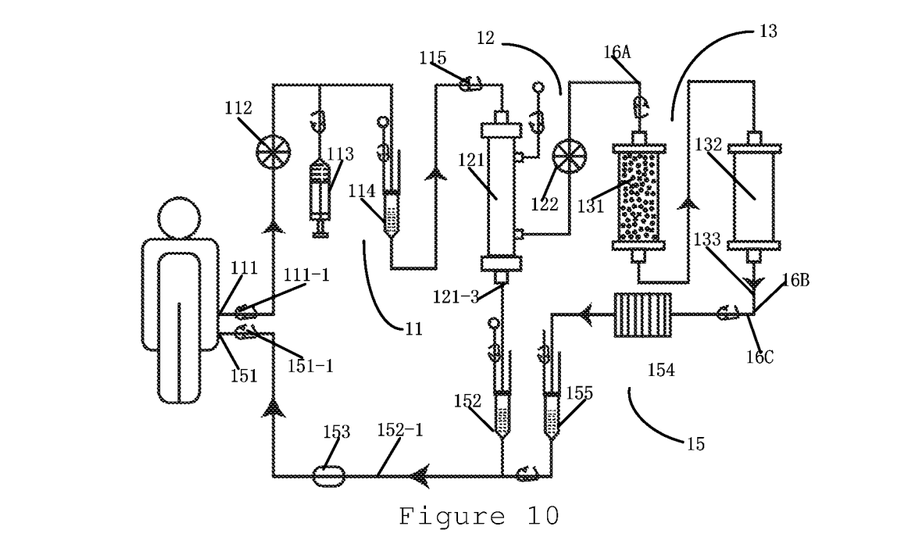
FIG. 10 is a schematic view of a non-biological purification mode of the combined biological artificial liver support system of the present invention.

1. Please refer to FIGS. 1, 3, 4, 6 and 10, of which FIG. 10 shows the non-biological purification mode of the support system 1. Close the pinch valve 163-2A of the first three-way device 16A of the support system 1, and open the pinch valve 163-1A; close the pinch valve 163-1B of the second three-way device 16B and open the pinch valve 163-2B; and close the pinch valve 163-1C of the third three-way device 16C and open the pinch valve 163-2C. By controlling the on-off of the branch of the flow restricting member (pinch valves, including the pinch valve 163-2A, pinch valve 163-1A, pinch valve 163-1B, pinch valve 163-2B, pinch valve 163-1C, and pinch valve 163-2C) on the branch of the three-way device 16, the support system 1 enters the non-biological purification mode.

In the non-biological purification mode, in the support system 1, the blood input branch tube 11, the first plasma separation branch tube 12, the non-biological purification branch tube 13, and the plasma return branch tube 15 participate in the non-biological purification mode. Plasma flows from the blood pump 112 into the blood input branch tube 11 through the blood input end 111, and the drug infusion device 113 injects heparin in parallel and they are uniformly mixed by the blood mixer 114. Under the power provided by the plasma separation pump 122, the blood passes through the first blood separator 121, and blood cells enter the blood cell mixer 152 through the blood cell outlet 121-3. The separated plasma flows out from the plasma outlet 121-2, and enters the plasma perfusion device 131 and bilirubin adsorber 132 through the valve 163-1A of the first three-way device 16A. The purified plasma passes through a first purification branch 133, passes through the valve 163-2B (or the valve 163-1C of the third three-way device 16C) of the second three-way device 16B, and enters the plasma return branch tube 15. Then the purified plasma is mixed with blood cells from the blood cell outlet 121-3 in the blood cell mixer 152 to form whole blood, and after being inspected by the bubble monitor 153, they return to the outside through the blood output end 151. After the above process, the non-biological purification process of blood is completed.

Figure 11:
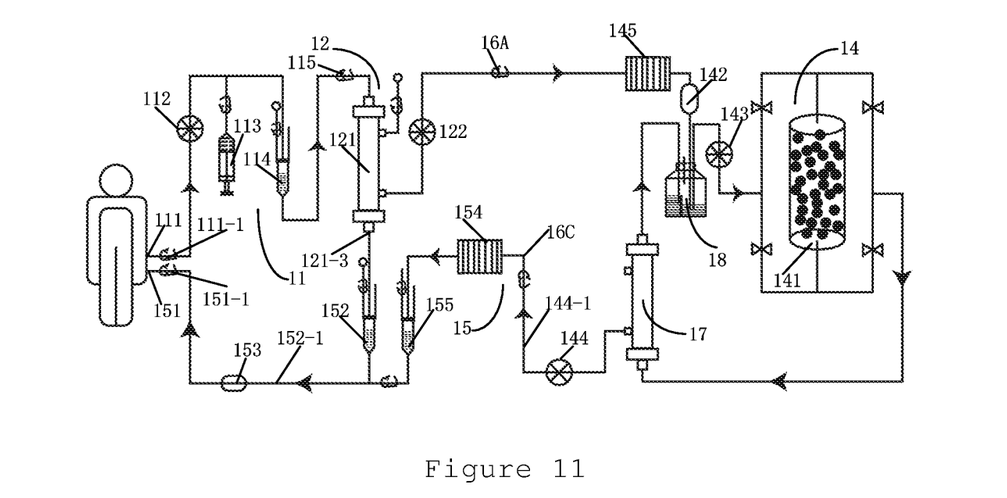
FIG. 11 is a schematic view of a biological purification mode of the combined biological artificial liver support system of the present invention.

2. Please refer to FIGS. 1, 3, 4, 6 and 11, of which FIG. 11 shows the biological purification mode of the support system 1. Open the pinch valve 163-2A of the first three-way device 16A of the support system 1, and close the pinch valve 163-1A; open the pinch valve 163-1B of the second three-way device 16B and close the pinch valve 163-2B; close the pinch valve 163-1C of the third three-way device 16C and open the pinch valve 163-2C. By turning on and off the control branch of the flow restricting member-pinch valve (including the pinch valve 163-2A, pinch valve 163-1A, pinch valve 163-1B, pinch valve 163-2B, pinch valve 163-1C, and pinch valve 163-2C) on the branch of the three-way device 16, the support system 1 enters the biological purification mode.

In the biological purification mode, in the support system 1, the blood input branch tube 11, the first plasma separation branch tube 12, the biological purification branch tube 14 and the plasma return branch tube 15 participate in the biological purification mode. Plasma flows from the blood pump 112 into the blood input branch tube 11 through the blood input port 111, and the drug infusion device 113 injects heparin in parallel and they are uniformly mixed by the blood mixer 114. Under the power provided by the plasma separation pump 122, the blood passes through the first blood separator 121, and the blood cells enter the blood cell mixer 152 through the blood cell outlet 121-3. The separated plasma flows out from the plasma outlet 121-2 and enters the oxygenator 142 of the biological purification branch tube 14 through the valve 163-2A of the first three-way device 16A. After the plasma is fully oxygenated in the oxygenator 142, it flows into the first chamber 181 of the liquid storage bottle 18 for temporary storage or waiting for flow rate adjustment. Under the power provided by the circulation pump 143, the plasma in the first chamber 181 enters the hepatocyte culture cartridge assembly 141 through the circulation branch 143.

The hepatocyte culture cartridge assembly 141 controls the valve assembly 141-2 to form two plasma flow modes: top-down flow and bottom-up flow.

In the valve assembly 141-2, the second valve 141-2B and the third valve 141-2C are closed, and the first valve 141-2A and the fourth valve 141-2D are kept open, thereby forming a top-down conduit. The plasma passes through the circulation branch 143-1, enters the first circulation tube 141-3A through the first interface 141-4A, and enters one end of the hepatocyte culture cartridge body 141-1 through the third interface 141-4C. In the hepatocyte culture cartridge body 141-1, the plasma fully reacts with the hepatocytes. The plasma after the reaction flows out from the other end of the hepatocyte culture cartridge body 141-1, flows into the fourth circulation tube 141-3D through the fourth interface 141-4D, and finally flows to the plasma return branch 144-1 through the second interface 141-4B.

In the valve assembly 141-2, the second valve 141-2B and the third valve 141-2C are opened, and the first valve 141-2A and the fourth valve 141-2D are kept closed to form a conduit that flows from bottom to top. The plasma passes through the circulation branch 143-1, enters the third circulation tube 141-3C through the first interface 141-4A, and enters an end of the hepatocyte culture cartridge body 141-1 through the fourth interface 141-4D. In the hepatocyte culture cartridge body 141-1, plasma fully reacts with hepatocytes. The reacted plasma flows out from the other end of the hepatocyte culture cartridge body 141-1, flows into the second circulation tube 141-3B through the third interface 141-4C, and finally flows to the plasma return branch 144-1 through the second interface 141-4B.

The alternating top-down flow and bottom-up flow are conducive to sufficient contact between plasma and hepatocytes, reducing the dead space in the hepatocyte culture cartridge body 141-1, and promoting the flow of substances in the culture cartridge assembly.

The biologically purified plasma enters the plasma return separation branch tube 15, and is mixed with the blood cells from the blood cell outlet 121-3 in the blood cell mixer 152 to form whole blood. After being inspected by the bubble monitor 153, they return to the outside through the blood output end 151. The blood undergoes the above process to complete the biological purification process.

Figure 12:
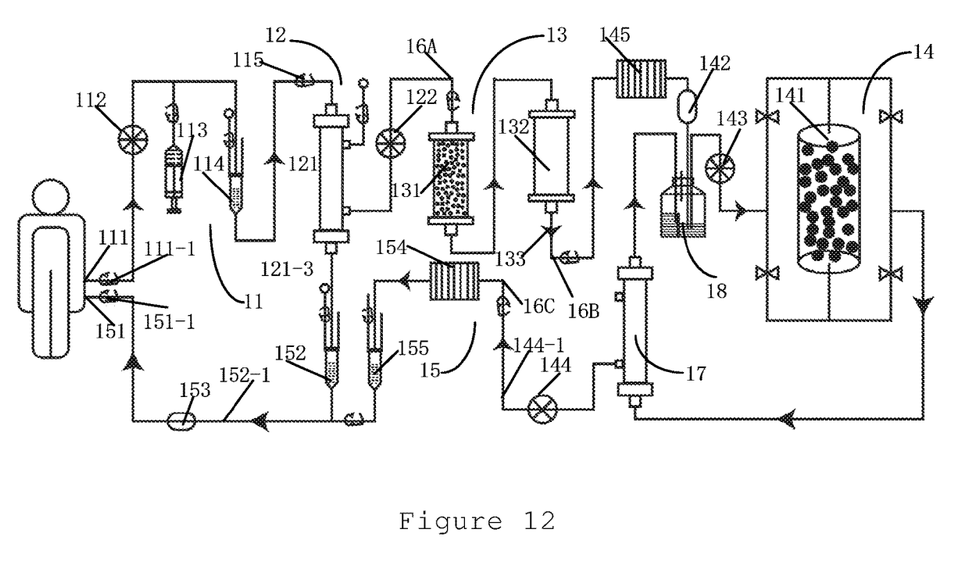
FIG. 12 is a schematic view of a mixing mode of the combined bio-artificial liver support system of the present invention.

3. Please refer to FIGS. 1, 3, 4, 6 and 12, of which FIG. 12 shows the mixing mode of the support system 1. Close the pinch valve 163-2A of the first three-way device 16A of the support system 1, and connect a downstream pipe of the pinch valve 163-2A to the pinch valve 163-1B, and open the pinch valve 163-1A; open the pinch valve 163-1B of the second three-way device 16B and close the pinch valve 163-2B; and close the pinch valve 163-1C of the third three-way device 16C and open the pinch valve 163-2C. The support system 1 enters the mixing mode by switching on and off the control branch of the flow restricting member—pinch valve (including pinch valve 163-2A, pinch valve 163-1A, pinch valve 163-1B, pinch valve 163-2B, pinch valve 163-1C, pinch valve 163-2C), of the three-way device 16.

In the mixing mode, in the support system 1, the blood input branch tube 11, the first plasma separation branch tube 12, the non-biological purification branch tube 13, the biological purification branch tube 14, and the plasma return branch tube 15 participate in the mixing purification mode. Plasma flows from the blood pump 112 into the blood input branch tube 11 through the blood input end 111, and the drug infusion device 113 injects heparin in parallel and they are uniformly mixed by the blood mixer 114. Under the power provided by the plasma separation pump 122, the blood passes through the first blood separator 121, and the blood cells enter the blood cell mixer 152 through the blood cell outlet 121-3. The separated plasma flows out from the plasma outlet 121-2, enters the plasma perfusion device 131 and enters the bilirubin adsorber 132 through the valve 163-1A of the first three-way device 16A. The purified plasma passes through the first purification branch 133, passes through the valve 163-2B of the second three-way device 16B (or the valve 163-1C of the third three-way device 16C), and enters the oxygenator 142 of the biological purification branch tube 14. After the plasma is fully oxygenated in the oxygenator 142, it flows into the first chamber 181 of the liquid storage bottle 18 for temporary storage or waiting for flow rate adjustment. Under the power provided by the circulation pump 143, the plasma in the first chamber 181 enters the hepatocyte culture cartridge assembly 141 through the circulation branch 143. For the blood plasma flow in the hepatocyte culture cartridge assembly 141, please refer to the blood plasma flow in the hepatocyte culture cartridge assembly 141 in the biological purification mode.

The mixed and purified plasma enters the plasma return branch tube 15, and is mixed with the blood cells from the blood cell outlet 121-3 in the blood cell mixer 152 to form whole blood. After being inspected by the bubble monitor 153, it returns to the outside through the blood output end 151. The blood undergoes the above process to complete the mixing purification process.

In the biological purification mode and the mixing mode of this embodiment, a second plasma separation branch tube 17 is also provided between the biological purification separation branch tube 14 and the plasma return branch tube 15. The plasma flowing out of the second interface 141-4B passes through the second plasma separator 17 to be separated again. The plasma enters the second plasma separator 17 through the second plasma inlet 171-1, and the re-separated plasma flows out from the second plasma outlet 171-2, and then enters the plasma return branch tube 15 through the plasma return pump 144. The plasma with blood cells enters the second chamber 182 of the liquid storage bottle 18 through the cell outlet 171-3, so as to settle the cells and cell debris, and continue to enter the circulation of the hepatocyte culture cartridge assembly 141.

This embodiment exemplarily describes the specific structure of the support system 1. The support system 1 of the present invention controls the on and off of different branch tubes through the three-way device 16 so that the support system 1 enters different modes, which facilitates the differentiated treatment of blood. In the present invention, by further adjusting the number and positions of the three-way devices 16, it is also possible to increase or decrease branch tubes with different functions, and further adjust the integrated functions of the support system 1.

The support system of the present invention also reasonably distributes the circulation tubes of the hepatocyte culture cartridge assembly 14 (including the first circulation tube 141-3A, the second circulation tube 141-3B, the third circulation tube 141-3C, and the fourth circulation tube 141-3D) and the on-off of the valve assembly 141-2 are reasonably controlled to realize two fluid flow modes in the hepatocyte culture cartridge assembly.

The above is only a part of the embodiments of the present invention. It should be noted that for those of ordinary skill in the art, without departing from the principles of the present invention, several improvements and retouches can be made, and these improvements and retouches should also be It is regarded as the protection scope of the present invention.

The invention claimed is:

1. A combined bio-artificial liver support system, comprising a plurality of branch tubes that are connected in sequence: a blood input branch tube, an upstream tail end of which is set as a blood input end, a first plasma separation branch tube comprising at least a first plasma separator, a non-biological purification branch tube comprising at least a plasma perfusion device and a bilirubin adsorber, a biological purification branch tube comprising at least a hepatocyte culture cartridge assembly, and a plasma return branch tube, a downstream tail end of which is set as a blood output end, wherein by means of three-way devices, the first plasma separation branch tube is connected to inlet ends of the biological purification branch tube and the non-biological purification branch tube, an outlet end of the non-biological purification branch tube is connected to the biological purification branch tube, and the outlet end of the non-biological purification branch tube is connected to the plasma return branch tube, each of the three-way devices comprises a three-way joint and branches respectively connected to the three-way joint, and at least two said branches are respectively provided with a flow restricting member and a coupling member.

2. The combined bio-artificial liver support system as recited in claim 1, wherein the non-biological purification branch tube comprises: the plasma perfusion device provided with a perfusion inlet and a perfusion outlet, the bilirubin adsorber connected to the perfusion outlet through a conduit, a first purification branch extending downstream from the bilirubin adsorber and a second three-way device among the three-way devices connected to an end of the first purification branch, the first purification branch is connected to the three-way joint of the second three-way device, and the remaining branches extending from the three-way joint are provided with the flow restricting members and the coupling members.

3. The combined bio-artificial liver support system as recited in claim 1, wherein the first plasma separation branch tube comprises: the first plasma separator provided with a blood inlet, a plasma outlet, and a blood cell outlet, and a plasma separation pump connected to the plasma outlet through a conduit, a plasma separation branch extending downstream from the plasma separation pump, and a first three-way device among the three-way devices connected to an end of the plasma separation branch, the plasma separation branch is directly connected to the three-way joint of the first three-way device, and the remaining branches extending from the three-way joint are provided with the flow restricting members and the coupling members.

4. The combined bio-artificial liver support system as recited in claim 3, wherein the plasma return branch tube comprises at least: a blood cell mixer connected to the blood cell outlet and provided with a whole blood outlet, and a bubble monitor connected to the whole blood outlet, the bubble monitor is also connected to the blood output end, and a third three-way device among the three-way devices is connected to an upstream end of the plasma return branch tube, the plasma return branch tube is directly connected to the three-way joint of the third three-way device, an upstream extension branch of the three-way joint of the third three-way device is connected to a first purification branch of the non-biological purification branch tube and a plasma return branch of the biological purification branch tube through the flow restricting member and the coupling members respectively.

5. The combined bio-artificial liver support system as recited in claim 1, wherein the biological purification branch tube comprises: an oxygenator provided with an oxygenation outlet, a circulation pump connected to the oxygenation outlet, and the hepatocyte culture cartridge assembly connected to the circulation pump through a circulation branch, a plasma return pump connected to the hepatocyte culture cartridge assembly, and a plasma return branch extending downstream from the plasma return pump.

6. The combined bio-artificial liver support system as recited in claim 5, wherein the hepatocyte culture cartridge assembly comprises a hepatocyte culture cartridge body and a circulation tube connected by a conduit and a valve assembly, an inlet of the circulation tube is connected to the circulation pump, and an outlet of the circulation tube is connected to the plasma return branch tube.

7. The combined bio-artificial liver support system as recited in claim 6, wherein the valve assembly comprises a first valve, a second valve, a third valve, and a fourth valve, the circulation tube includes a first circulation tube connected to the first valve, a second circulation tube connected to the second valve, a third circulation tube connected to the third valve, and the fourth circulation tube connected to the fourth valve, the first circulation tube and the second circulation tube are connected through a first interface, and the first interface is connected to the circulation branch, the third circulation tube and the fourth circulation tube are connected through a second interface, and the second interface is connected to the plasma return pump, the first circulation tube and the third circulation tube are connected through a third interface, and the third interface is connected to one end of the hepatocyte culture cartridge assembly, the second circulation tube and the fourth circulation tube are connected through a fourth interface, and the fourth interface is connected to the other end of the hepatocyte culture cartridge assembly.

8. The combined bio-artificial liver support system as recited in claim 7, wherein the fluid flow directions of the third interface and the fourth interface are opposite.

9. The combined bio-artificial liver support system as recited in claim 1, wherein a second plasma separation branch tube is further provided between the biological purification branch tube and the plasma return branch tube, the second plasma separation branch tube includes at least a second plasma separator provided with a second plasma inlet, a second plasma outlet, and a cell outlet, the second plasma inlet is connected to the hepatocyte culture cartridge assembly, and the second plasma outlet is connected to the plasma return branch tube.

10. The combined bio-artificial liver support system as recited in claim 9, wherein the cell outlet is connected to a liquid storage bottle for depositing cells or cell debris and flow rate difference adjustment, and the liquid storage bottle is also connected to the oxygenation outlet and the inlet of circulation pump.

11. The combined bio-artificial liver support system as recited in claim 10, wherein the cell outlet is connected to a second chamber of the liquid storage bottle, and a partition is provided between a first chamber and the second chamber for isolating the deposited cells and cell debris.

12. The combined bio-artificial liver support system as recited in claim 1, wherein the branches of the three-way devices and the branch tubes connected to the three-way devices are connected by at least one of connection modes of screw connection assembly connection and sleeve member connection.

13. The combined bio-artificial liver support system as recited in claim 12, wherein the connection structure of the screw connection assembly comprises: the branches tapped with an external thread, and a conduit of the branch tube tapped with an internal thread matching the external thread at one end.

14. The combined bio-artificial liver support system as recited in claim 13, wherein a connection location between the conduit and the branch is also provided with a sleeve which provides resistance for rotation of the branch tube and the branch and enhances the sealing performance.

* * * * *